US011457934B2

(12) United States Patent
Dutoit et al.

(10) Patent No.: US 11,457,934 B2
(45) Date of Patent: Oct. 4, 2022

(54) INTRAMEDULLARY NAIL WITH WIRE OR MAGNET FOR TARGETING OF A BONE-ANCHOR LOCKING HOLE

(71) Applicant: DePuy Synthes Products, Inc., Raynham, MA (US)

(72) Inventors: Christof Dutoit, Solothurn (CH); René Haag, Berwyn, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 16/043,352

(22) Filed: Jul. 24, 2018

(65) Prior Publication Data
US 2020/0029980 A1 Jan. 30, 2020

(51) Int. Cl.
| A61B 17/17 | (2006.01) |
| A61B 17/72 | (2006.01) |
| A61B 17/56 | (2006.01) |
| A61B 17/00 | (2006.01) |

(52) U.S. Cl.
CPC ...... *A61B 17/1707* (2013.01); *A61B 17/7233* (2013.01); *A61B 2017/0011* (2013.01); *A61B 2017/00039* (2013.01); *A61B 2017/00526* (2013.01); *A61B 2017/00876* (2013.01); *A61B 2017/00929* (2013.01); *A61B 2017/564* (2013.01)

(58) Field of Classification Search
CPC .............. A61B 17/72–7291; A61B 17/74–748
USPC .................................................... 606/62–68
See application file for complete search history.

(56) References Cited

U.S. PATENT DOCUMENTS

| 5,127,913 | A | * | 7/1992 | Thomas, Jr. ....... A61B 17/1707 606/62 |
| 5,411,503 | A | * | 5/1995 | Hollstien ........... A61B 17/1707 606/80 |
| 5,433,720 | A | | 7/1995 | Faccioli et al. |
| 5,540,691 | A | | 7/1996 | Elstrom et al. |
| 5,584,838 | A | | 12/1996 | Rona et al. |
| 5,707,375 | A | | 1/1998 | Durham et al. |
| 6,162,228 | A | | 12/2000 | Durham |
| 6,503,249 | B1 | | 1/2003 | Krause |
| 6,697,664 | B2 | | 2/2004 | Kienzle, III et al. |
| 7,060,075 | B2 | | 6/2006 | Govari et al. |

(Continued)

FOREIGN PATENT DOCUMENTS

| AU | 2003213476 B2 | 11/2008 |
| CA | 2500845 C | 7/2012 |

(Continued)

*Primary Examiner* — Nicholas J Plionis
(74) *Attorney, Agent, or Firm* — BakerHostetler

(57) ABSTRACT

In one embodiment, an intramedullary nail has a body that includes proximal and distal ends and an inner surface that defines at least one locking hole that extends into an outer surface of the body so as to receive a bone anchor to lock the nail in a medullary canal of a bone. The body has a first biocompatible material that defines at least a portion of the outer surface. The nail has a second material that is different from, and at least partially encapsulated in, the first material. The second material can produce at least one of an electrical current and a magnetic field, and is supported by the nail body such that a position of the at least one bone-anchor locking hole can be detected based on the at least one of the electrical current and the magnetic field.

19 Claims, 9 Drawing Sheets

(56) References Cited

U.S. PATENT DOCUMENTS

| | | | |
|---|---|---|---|
| 7,686,818 B2 | 3/2010 | Simon et al. | |
| 7,727,240 B1 | 6/2010 | Benton | |
| 7,753,913 B2 | 7/2010 | Szakelyhidi et al. | |
| 8,444,653 B2 | 5/2013 | Nycz et al. | |
| 8,623,023 B2 | 1/2014 | Ritchey et al. | |
| 8,739,801 B2 | 6/2014 | Rains et al. | |
| 8,814,868 B2 | 8/2014 | Janna et al. | |
| 9,492,210 B2* | 11/2016 | Rains | A61B 17/72 |
| 9,539,037 B2 | 1/2017 | Janna et al. | |
| 10,357,292 B2* | 7/2019 | Rains | A61B 90/39 |
| 2005/0096655 A1 | 5/2005 | Trinchese | |
| 2006/0052782 A1* | 3/2006 | Morgan | A61B 90/06 606/60 |
| 2009/0299376 A1 | 12/2009 | Martinez et al. | |
| 2010/0145337 A1* | 6/2010 | Janna | A61B 17/1725 606/67 |
| 2010/0274256 A1* | 10/2010 | Ritchey | A61B 5/05 606/96 |
| 2011/0118594 A1 | 5/2011 | Srivastava et al. | |
| 2011/0282395 A1* | 11/2011 | Beyar | A61B 17/7233 606/301 |
| 2012/0059376 A1* | 3/2012 | Rains | A61B 17/80 606/62 |
| 2012/0226094 A1* | 9/2012 | Ritchey | A61B 34/20 600/12 |
| 2012/0259346 A1* | 10/2012 | Hansen | A61B 17/0057 606/138 |
| 2013/0018381 A1 | 1/2013 | Baumgartner | |
| 2013/0218007 A1 | 8/2013 | Petteys et al. | |
| 2013/0281884 A1 | 10/2013 | Mullaney et al. | |
| 2013/0325007 A1* | 12/2013 | Beyar | A61B 17/7208 606/62 |
| 2014/0081121 A1* | 3/2014 | Wilhelm | A61B 17/80 600/409 |
| 2014/0135769 A1* | 5/2014 | Ziran | A61B 17/72 606/63 |
| 2014/0163557 A1 | 6/2014 | Beyar et al. | |
| 2014/0246809 A1 | 9/2014 | Hofmann et al. | |
| 2015/0034604 A1 | 2/2015 | Subramanian et al. | |
| 2015/0297303 A1 | 10/2015 | Heindl et al. | |
| 2016/0058321 A1 | 3/2016 | Ritchey et al. | |
| 2017/0027624 A1* | 2/2017 | Wilson | C22F 1/183 |
| 2017/0035469 A1 | 2/2017 | Rains et al. | |
| 2019/0046273 A1* | 2/2019 | Mikuszeit | A61B 34/20 |
| 2019/0175232 A1* | 6/2019 | Karg | A61B 17/7233 |

FOREIGN PATENT DOCUMENTS

| | | |
|---|---|---|
| CN | 105792736 A | 7/2016 |
| EP | 1847227 B1 | 11/2008 |
| EP | 1589883 B1 | 12/2010 |
| EP | 2667799 B1 | 7/2016 |
| EP | 3042621 B1 | 8/2017 |
| WO | 1997013467 A1 | 4/1997 |
| WO | 2001034016 A3 | 5/2001 |
| WO | 2005120203 A3 | 2/2007 |
| WO | 2007124731 A2 | 11/2007 |
| WO | 2009032969 A1 | 3/2009 |
| WO | 2012051512 A1 | 4/2012 |
| WO | 2017011244 A1 | 1/2017 |

* cited by examiner

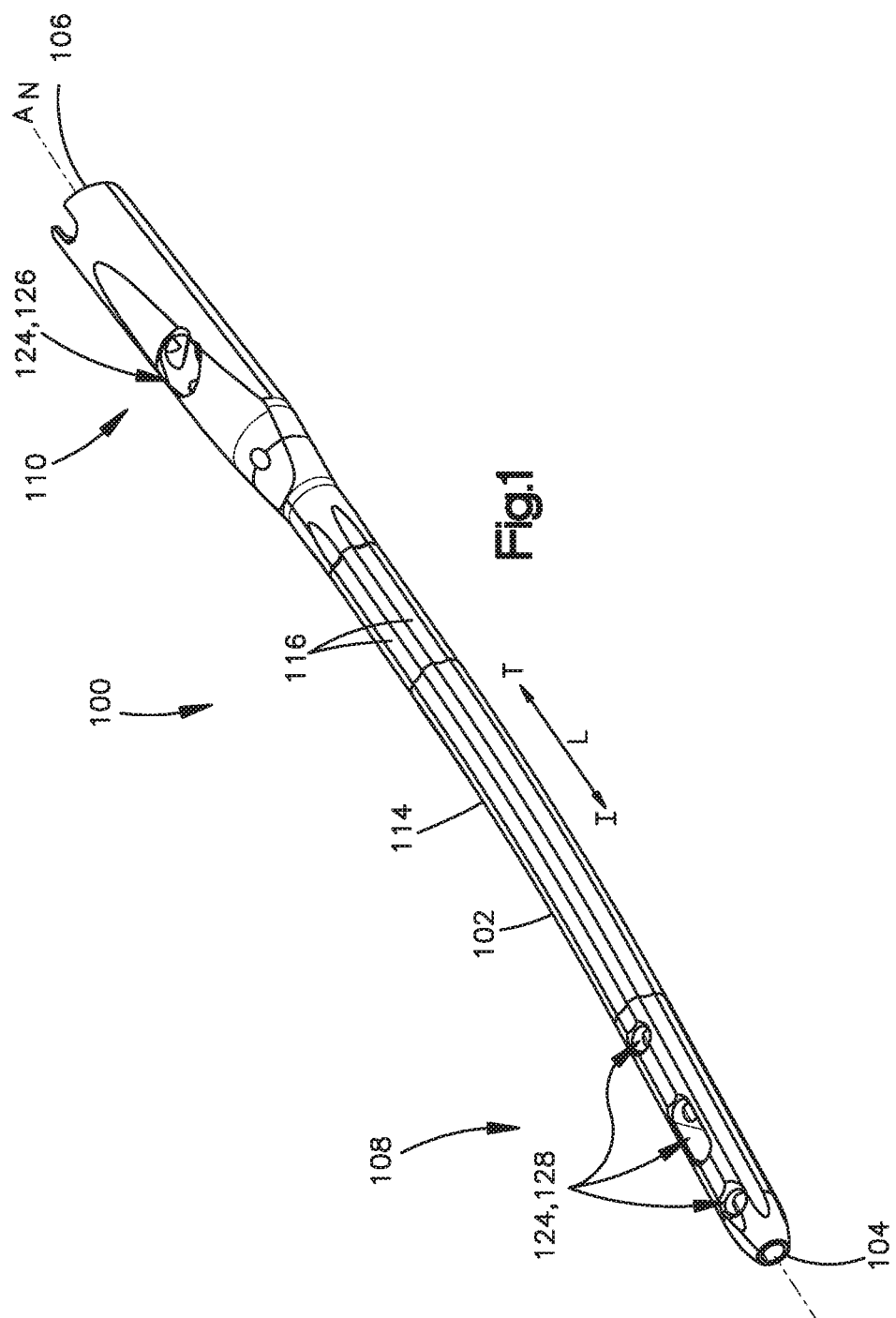

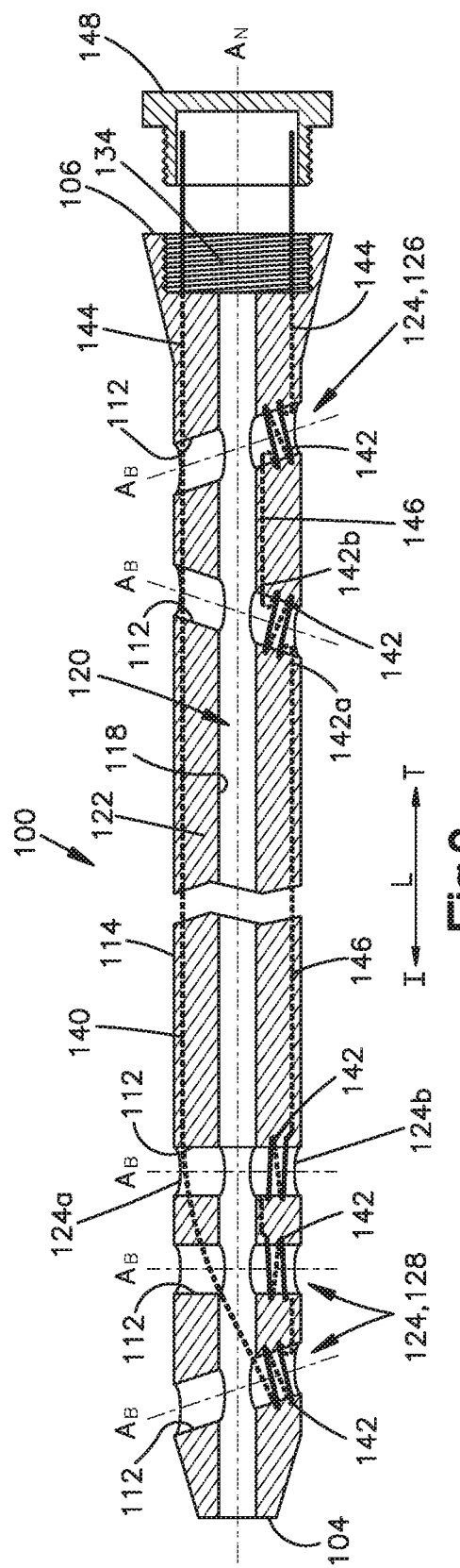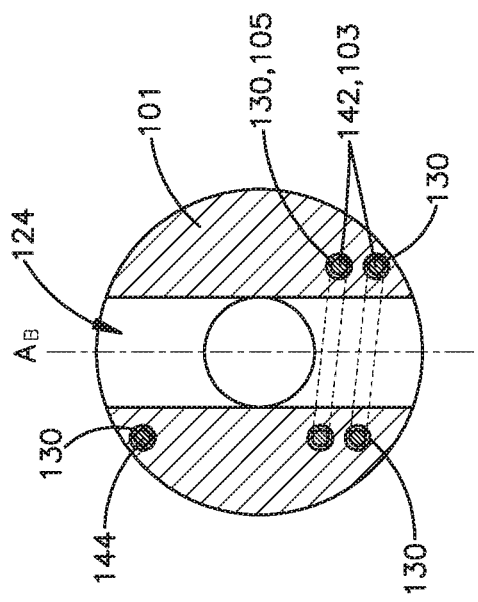

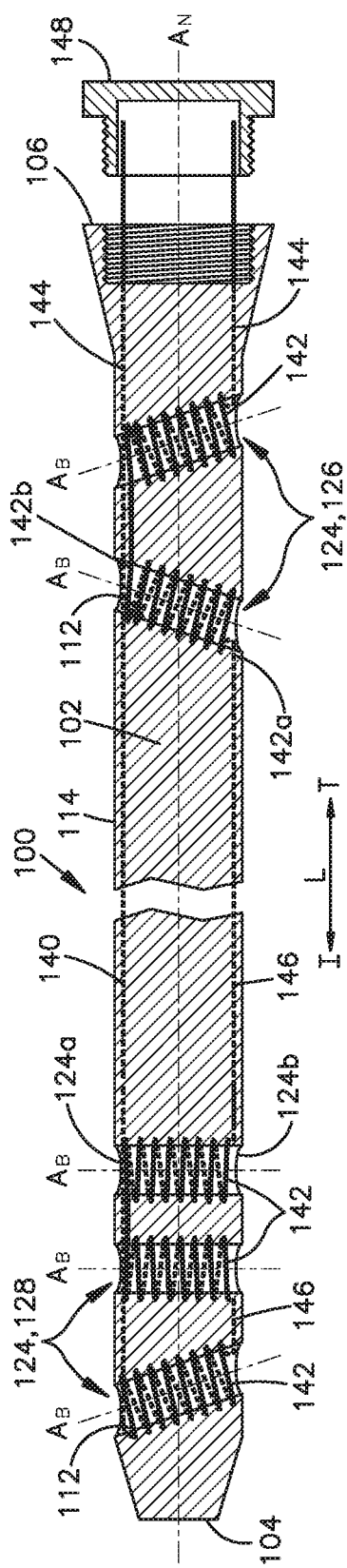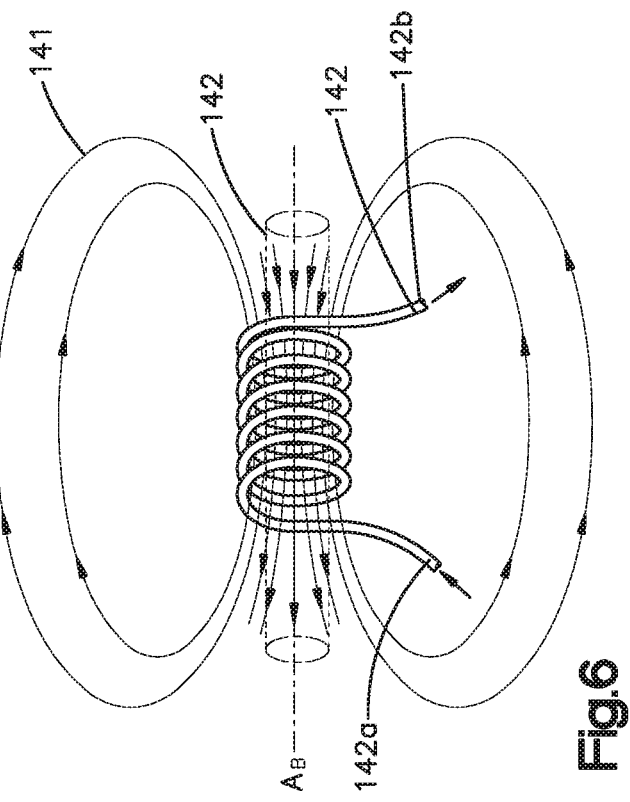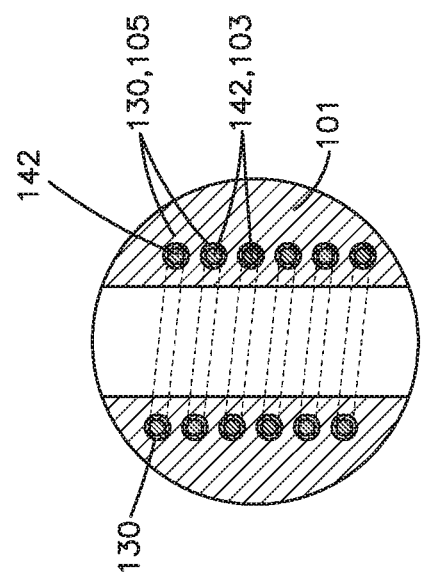

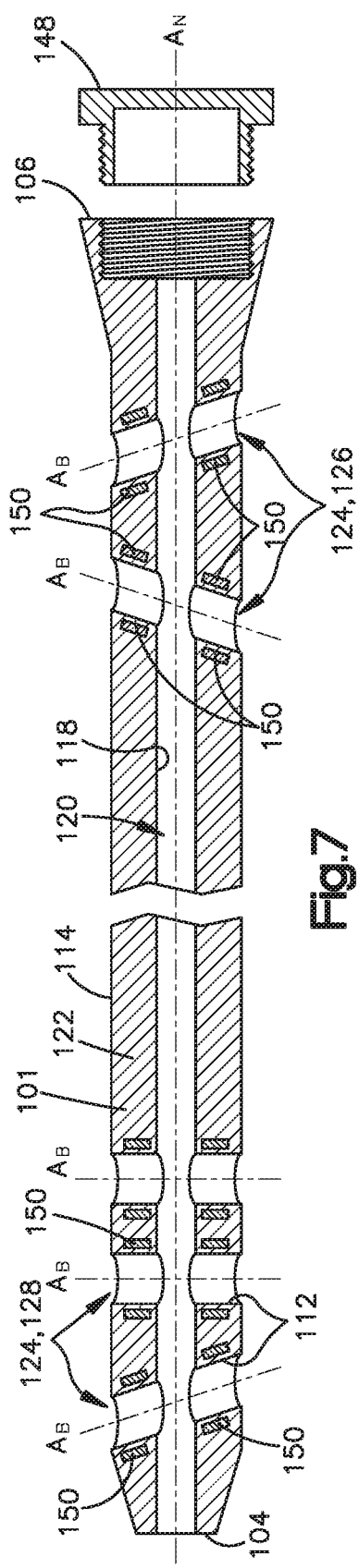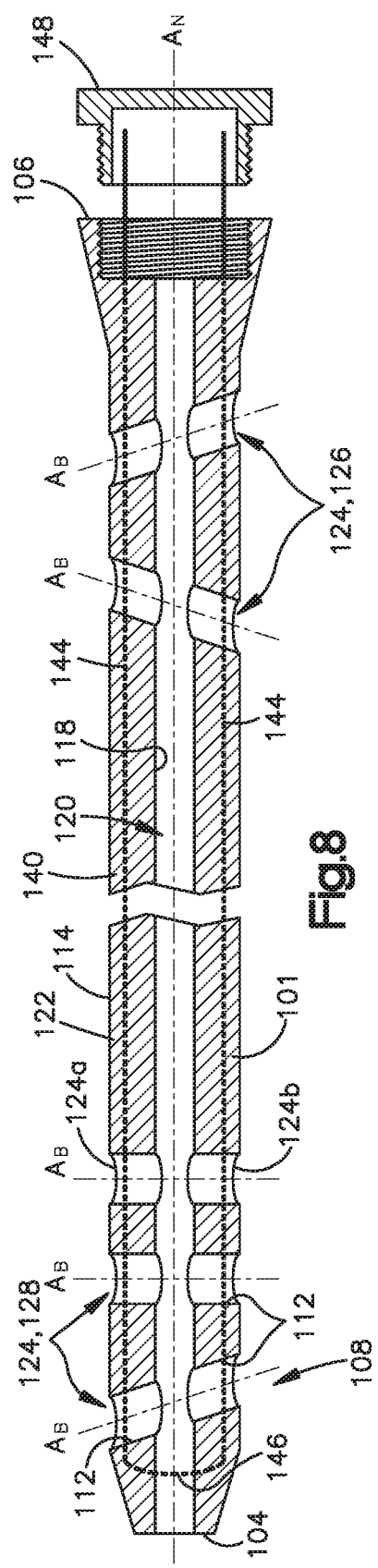

INTRAMEDULLARY NAIL WITH WIRE OR MAGNET FOR TARGETING OF A BONE-ANCHOR LOCKING HOLE

TECHNICAL FIELD

The present disclosure relates to systems, assemblies, and methods for the insertion and fixation of a nail into an intramedullary canal of a bone.

BACKGROUND

Intramedullary nails are commonly used to treat fractures in long bones of the body such as fractures in femurs, tibias, and humeri, fibulas, radii, or ulnas. To treat such fractures, the intramedullary nail is inserted into a medullary canal of the long bone such that the nail spans across one or more fractures to fragments of the long bone that are separated by the one or more fractures. Bone anchors are then inserted through the bone and into the intramedullary nail at opposing sides of the fracture, thereby fixing the intramedullary nail to the bone. The intramedullary nail can remain in the medullary canal at least until the fracture is fused.

SUMMARY

In an example embodiment, an intramedullary nail is sized and configured to be implanted into a medullary canal of a bone. The intramedullary nail comprises a nail body having a proximal end, a distal end, an outer surface, and an inner surface. The proximal and distal ends are offset from one another such that the nail body is elongate from the proximal end to the distal end. The outer surface extends from the proximal end to the distal end such that the outer surface defines a perimeter of the intramedullary nail. The inner surface that defines at least one bone-anchor locking hole that extends into the outer surface and that is configured to receive a bone anchor to lock the intramedullary nail in the medullary canal. The nail body has a first material that is biocompatible and that defines at least a portion of the perimeter of the intramedullary nail. Further, the intramedullary nail comprises a second material that is at least partially encapsulated in the first material. The second material is different from the first material and is configured to produce at least one of an electrical current and a magnetic field. The second material is supported by the nail body such that a position of the at least one bone-anchor locking hole can be detected based on the at least one of the electrical current and the magnetic field.

Another example embodiment includes a method of implanting an intramedullary nail into a bone. The method comprises a step of inserting the intramedullary nail is inserted into a medullary canal of the bone such that the intramedullary nail is elongate along the medullary canal from a proximal end of the intramedullary nail to a distal end of the intramedullary nail. The method comprises a step of sensing at least one of an electrical current and a magnetic field produced by the intramedullary nail. The method comprises a step of detecting a location of a select bone-anchor locking hole that extends into the intramedullary nail based on the at least one of an electrical current and a magnetic field. The method comprises a step of aligning a cutting instrument with the select locking hole based on the detected location. The method comprises a step of forming a bore in the bone with the cutting instrument such that the bore extends to the select bone-anchor locking hole. The method comprises a step of inserting a bone anchor through the bore and into the select bone-anchor locking hole so as to secure the intramedullary nail to the bone.

Another example embodiment includes a method of fabricating an intramedullary nail that is sized and configured to be implanted into a medullary canal of a bone. The method comprises a step of forming a nail body from a first material that is biocompatible such that the nail body has a proximal end, a distal end that is offset from the proximal end, an outer surface that extends from the proximal end to the distal end, and an inner surface that defines at least one bone-anchor locking hole that extends into the outer surface and that is configured to receive a bone anchor to lock the intramedullary nail in the medullary canal. The method comprises a step of at least partially encapsulating a magnet or electrically conductive wire formed from a second material, different from the first material, in the nail body such that, when at least one of an electrical current and a magnetic field is produced by the magnet or electrically conductive wire, a position of the at least one bone-anchor locking hole can be detected based on the at least one of the electrical current and the magnetic field.

BRIEF DESCRIPTION OF THE DRAWINGS

The following description of the illustrative embodiments may be better understood when read in conjunction with the appended drawings. It is understood that potential embodiments of the disclosed systems and methods are not limited to those depicted.

FIG. 1 shows a perspective view of an intramedullary nail according to one embodiment;

FIG. 2 shows a schematic representation of a cross-sectional side view of an intramedullary nail according to one embodiment having a cannulation and a plurality of bone-anchor locking holes at least partially surrounded by coils;

FIG. 3 shows a schematic representation of a cross-sectional end view of the intramedullary nail of FIG. 2;

FIG. 4 shows a schematic representation of a cross-sectional side view of an intramedullary nail according to another embodiment that is devoid of a cannulation and has a plurality of bone-anchor locking holes at least partially surrounded by coils;

FIG. 5 shows a schematic representation of a cross-sectional end view of the intramedullary nail of FIG. 4;

FIG. 6 shows a schematic representation of a magnetic field generated at a bone-anchor locking hole of the intramedullary nail of FIG. 1;

FIG. 7 shows a schematic representation of a cross-sectional side view of an intramedullary nail according to yet another embodiment having a plurality of bone-anchor locking holes at least partially surrounded by permanent magnets;

FIG. 8 shows a schematic representation of a cross-sectional side view of an intramedullary nail according to yet another embodiment having at least one wire embedded in the nail;

DETAILED DESCRIPTION OF ILLUSTRATIVE EMBODIMENTS

Figure 9:
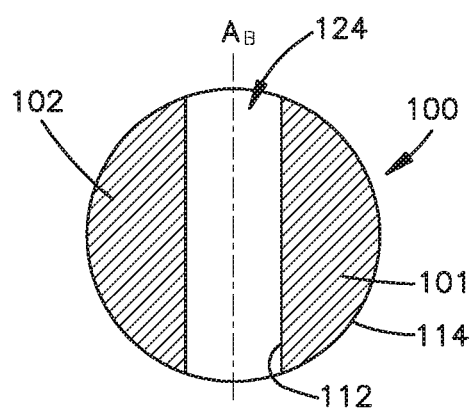
FIG. 9 shows a cross-sectional end view of an intramedullary nail according to one example embodiment before an electrically conductive wire or magnet is encapsulated therein.

Commonly, an intramedullary nail is implanted by driving the nail into a medullary canal of a long bone such as a tibia, fibula, humerus, femur, radius, or ulna. The nail is then secured to the bone by inserting bone anchors through the bone and into bone-anchor locking holes that are located at a proximal end and a distal end of the intramedullary nail. Once inside the medullary canal, the bone obstructs the surgeon's view of the bone-anchor locking holes, thereby complicating the insertion of the bone anchors into the locking holes. To further complicate matters, the intramedullary nail may bend as it is driven into the medullary canal such that a position of each locking hole at the distal end of the nail may change relative to the proximal end of the nail. The amount that the nail bends can vary depending upon the anatomy of the patient (e.g., the path of the medullary canal). As a result, the position of the distal locking hole or holes may vary from one implantation to the next.

To overcome these challenges, various tools have been developed to align the bone anchors with the locking holes. These tools include, for example, aiming guides that are attached to the nail, and magnetic nail alignment probes that are inserted into a cannulation of the nail to a position that is adjacent a locking hole. However, use of these alignment tools often require setup and calibration, which can be time consuming. Further, some alignment tools require the use of x-ray, thereby exposing the patient to radiation. In procedures that require distal locking (i.e., inserting a bone anchor into a distal bone-anchor locking hole) before proximal locking (i.e., inserting a bone anchor into a proximal bone-anchor locking hole) such as implantation of retrograde femoral and humeral nails, the distal bone anchor is inserted before the proximal bone anchor. As a result, the proximal bone anchor does not obstruct access to a cannulation in the nail. However, in procedures that require proximal locking before distal locking such as implantation of antegrade femoral and tibial nails, the proximal bone anchor can obstruct access to a cannulation in the nail. Consequently, nail alignment probes cannot be inserted into the cannulation to support distal locking after proximal locking.

As an alternative, and as will be discussed below, an intramedullary nail can be implemented with features that can assist a surgeon in locating the locking holes for insertion of bone anchors. These features can include, for example, at least one of (i) a wire that is configured to carry a current, and (ii) a magnet. In at least some embodiments, the bone anchors can be inserted into at least the distal locking holes, and optionally the proximal locking holes, without a need for an aiming guide and/or without a need to calibrate an alignment tool. Further, in at least some embodiments, proximal and distal locking can be performed without needing access to the cannulation. Therefore, in such embodiments, the intramedullary nail can provide a surgeon with the option of performing proximal locking before distal locking or performing distal locking before proximal locking.

Referring generally to FIGS. 1 to 8, an intramedullary nail 100 comprises a nail body 102 having a distal end 104 and a proximal end 106 that are offset from one another. The distal end 104 can be considered to be an insertion end or leading end, and can define a first terminal or outermost end of the nail body 102. For example, the distal end 104 can be the end that is furthest from the surgeon during insertion of the nail 100. The proximal end 106 can be considered to be a trailing end and can define a second terminal or outermost end of the nail body 102. For example, the proximal end 106 can be the end that is closest to the surgeon during insertion of the nail 100. The intramedullary nail 100 has an outer surface 114 that extends from the proximal end 106 to the distal end 104 such that the outer surface 114 defines a perimeter of the intramedullary nail 100. The intramedullary nail 100 has at least one inner surface 112 that defines at least one bone-anchor locking hole 124 that extends into the outer surface 112 and that is configured to receive a bone anchor to lock the intramedullary nail 100 in a medullary canal of a bone. The intramedullary nail 100 comprises a first material 101 that is biocompatible and that defines at least a portion of the perimeter of the intramedullary nail 100. The intramedullary nail 100 further comprises a second material 103 that is different from the first material 101. The second material 103 is at least partially encapsulated in the first material 101 and is configured to produce at least one of an electrical current and a magnetic field. In some embodiments, the second material can be completely encapsulated in the first material 101. The second material 103 can define at least one of a wire and a magnet. The second material 103 is supported by the nail body 102 such that a position of the at least one bone-anchor locking hole 124 can be detected based on the at least one of the electrical current and the magnetic field.

Referring more specifically to FIG. 1, the nail body 102 is elongate from the proximal end 106 to the distal end 104. For instance, the nail body 102 is substantially elongate along a central pathway that extends from the proximal end 106 to the distal end 104. In at least some embodiments, the central pathway can be defined by a central axis $A_N$ of the nail body 102 that extends from the proximal end 106 to the distal end 104. It will be appreciated that the central pathway and/or central axis $A_N$ of the nail body 102 can be straight or curved. Thus, the nail body 102 can be straight or curved as it extends along the central pathway and/or central axis $A_N$ from the proximal end 106 to the distal end 104. The intramedullary nail 100 can be inserted into a medullary canal of a long bone such that the central pathway and/or central axis $A_N$ extends along the length of the medullary canal.

The nail body 102 has a leading portion 108 and a trailing portion 110 that are offset from one another. The leading portion 108 can extend from the distal end 104 of the nail body 102 towards the proximal end 106 along a trailing direction T. Further, the trailing portion 110 can extend from the proximal end 106 towards the distal end 104 along an insertion direction I, opposite the trailing direction T. It will be understood that the insertion direction I extends from the proximal end 106 towards the distal end 104, and the trailing direction T extends in a direction opposite the insertion direction I (i.e., from the distal end 104 towards the proximal end 106).

In at least some embodiments, the trailing portion 110 has a length that is less than or equal to one half of an overall length of the intramedullary nail 100. In at least some such embodiments, the trailing portion 110 has a length that is less than or equal to one third or one quarter of the overall length of the intramedullary nail 100. Additionally or alternatively, in at least some embodiments, the leading portion 108 has a length that is less than or equal to one half of the overall length of the intramedullary nail 100. In at least some such embodiments, the leading portion 108 has a length that is less than or equal to one third or one quarter of an overall length of the intramedullary nail 100.

The outer surface 114 extends between the proximal end 106 and the distal end 104. For instance, the outer surface 114 can extend from the proximal end 106 to the distal end 104. The outer surface 114 can define the outer-most perimeter of the intramedullary nail 100. At least a portion, up to an entirety, of the outer surface 114 can be formed from a first material 101 that is biocompatible. The first material 101 can be, for example, any suitable implant grade material having suitable strength and elasticity to promote bone healing such as (without limitation) titanium alloy or stainless steel. The outer surface 114 can have any suitable cross-sectional shape as desired. For example, the outer surface 114 can be substantially circular in cross section along a plane that is substantially perpendicular to the central pathway and/or central axis $A_N$. Additionally or alternatively, the nail body 102 can define a plurality of recesses 116 that extend into the outer surface 114. The recesses 116 can be spaced circumferentially from one another around the outer perimeter of the nail body 102 and can be elongate as they extend along the insertion and/or trailing directions in accordance with the illustrated embodiments.

In some embodiments, as shown in FIGS. 2, 7, and 8, the intramedullary nail 100 can have an interior surface 118 opposite the outer surface 114. Thus, the nail body 102 can define a tubular wall 122 between the interior surface 118 and the outer surface 114. The interior surface 118 can define a cannulation 120 that extends into the proximal end 106 in the insertion direction I. The cannulation 120 can extend to the leading portion 108. For example, the cannulation 120 can extend through the distal end 104. Alternatively, the cannulation 120 can terminate prior to the distal end 104. The interior surface 118 can have a plurality of cross-sections along the central pathway and/or central axis $A_N$, each cross-section defined in a plane that is perpendicular to the central pathway and/or central axis $A_N$. The interior surface 118 in each cross-section can have any suitable cross-sectional shape as desired. For example, the interior surface 118 in each cross-section can define a cross-sectional shape that is closed such as a circle, oval, square, rectangle, or other shape. In alternative embodiments, as shown in FIG. 4, the intramedullary nail 100 can be solid along its central axis $A_N$ such that the intramedullary nail 100 is devoid of a cannulation.

The intramedullary nail 100 includes at least one inner surface 112 that defines the at least one bone-anchor locking hole 124. For example, the nail body 102 can have a plurality of inner surfaces 112, each defining a bone-anchor locking hole 124. In some embodiments, one or more, up to all, of the at least one inner surface 112 can be formed from the first material 101. Each bone-anchor locking hole 124 extends into the outer surface 114 of the nail 100. Each bone-anchor locking hole 124 is configured to receive a bone anchor that extends through the bone-anchor locking hole 124 so as to attach the intramedullary nail 100 to a bone. Each bone-anchor locking hole 124 can extend partially or entirely through the intramedullary nail 100. For instance, each bone-anchor locking hole 124 can extend into the outer surface 114 on a first side of the nail body 102 and out of the outer surface 114 on a second side of the nail body 102, opposite the first side. Thus, each bone-anchor locking hole 124 can extend from an opening 124a on a first side of the nail body 102 to an opening 124b on the second side of the nail body 102. In embodiments that have a cannulation, such as in FIGS. 2, 7, and 8, at least some of the bone-anchor locking holes 124 can extend through the tubular wall 122 on a first side of the nail body 102 and through the tubular wall 122 on a second side of the nail body 102, opposite the first side.

Each bone-anchor locking hole 124 extends through the nail body 102 along a central bone-anchor axis $A_b$ (see e.g., FIG. 2) that is angled with respect to the central pathway and/or the central axis $A_N$. For example, the central axis $A_N$ can be said to extend along a first direction, and each bone-anchor locking hole 124 can be said to extend into the nail body along a central axis $A_B$ that extends along a second direction, where the second direction forms a non-zero angle with the first direction. In some embodiments, each central axis $A_B$ can extend along a right angle or an oblique angle with the central pathway and/or the central axis $A_N$. Each bone-anchor locking hole 124 can be unthreaded or can include internal threading to receive external threading of a bone anchor. In some embodiments, one or more, up to all, of the central axes $A_B$ of the at least one bone-anchor locking hole 124 can intersect the central pathway and/or the central axis $A_N$.

The at least one bone-anchor locking hole 124 can include at least one proximal bone-anchor locking hole 126. Each of the at least one proximal bone-anchor locking hole 126 extends into the trailing portion 110 of the nail body 102. In some embodiments, each of the at least one proximal bone-anchor locking hole 126 extends into the nail body 102 at a distance from the distal end 106 that is less than or equal to one half of the overall length of the intramedullary nail 100, while in other embodiments, each of the at least one proximal bone-anchor locking hole 126 extends into the nail body 102 at a distance from the distal end 106 that is less than or equal to one third or one quarter of the overall length of the intramedullary nail 100. Although only one proximal bone-anchor locking hole 126 is shown in FIG. 1, it will be understood that the nail body 102 can define a plurality of proximal bone-anchor locking holes 126. For example, FIGS. 2, 4, 7, and 8 each show a plurality of proximal bone-anchor locking holes 126. In such embodiments, the plurality of proximal bone-anchor locking holes 126 can be offset from one another along a longitudinal direction L that extends between the distal end 104 and the proximal end 106.

The at least one bone-anchor locking hole 124 can additionally or alternatively include at least one distal bone-anchor locking hole 128. All of the at least one distal bone-anchor locking holes 128 are offset from all of the at least one proximal bone-anchor locking holes 126 along the longitudinal direction L. Each of the at least one distal bone-anchor locking hole 128 extends into the leading portion 108 of the nail body 102. In some embodiments, each of the at least one distal bone-anchor locking hole 128 extends into the nail body 102 at a distance from the distal end 104 that is less than or equal to one half of the overall length of the intramedullary nail 100. In some such embodiments, each of the at least one distal bone-anchor locking hole 128 can extend into the nail body 102 at a distance from the distal end 104 that is less than or equal to one third or one quarter of the overall length of the intramedullary nail 100. Although a plurality of distal bone-anchor locking holes 128 is shown, it will be understood that the nail body 102 can define as few as one distal bone-anchor locking hole 128. In embodiments having a plurality of distal bone-anchor locking holes 128, the plurality of distal bone-anchor locking holes 128 can be offset from one another along the longitudinal direction L. The central axes $A_B$ of one or more, up to all, of the bone-anchor locking holes 124 can lie in a common plane with one another. Alternatively, the central axes $A_B$ of one or more, up to all, of the bone-anchor locking holes 124 can lie in a different plane from one another.

Turning more specifically to FIGS. 2 to 6, an intramedullary nail 100 can include at least one wire 140 that is configured to carry an electrical current. The at least one wire 140 can be supported by the nail body 102 such that a position of the at least one bone-anchor locking hole can be determined based on the flow of an electrical current through the wire 140. The wire 140 can be formed of a second material 103, different from the first material 101. The second material 103 can be an electrically conductive material such as copper or other suitable electrically conductive material. The second material 103 can be formed of a non-biocompatible material if the second material 103 is encapsulated within the first material 101 so as to prevent the second material 103 from coming into contact with patient. Thus, the first material 101 can at least partially surround the second material 103. Alternatively, the second material 103 can be biocompatible material if the second material 103 is exposed such that the second material 103 might come into contact with the patient. In some embodiments, the second material 103 can be integral and monolithic with the first material 101 or with a third material (e.g., 105 in FIG. 3) that is integral and monolithic with the first material 101. In other embodiments, the intramedullary nail 100 can include an insert (see e.g., 152 in FIGS. 13 and 14) that comprises the second material 103 and can be disposed in the intramedullary nail 100.

In at least some embodiments, the intramedullary nail 100 can comprise a third material 105, different from the first and second materials. The third material 105 can be an electrically insulative material. Thus, the third material 105 can have an electrical conductivity that is less than that of the second material 103, and optionally, less than that of the first material 101. The intramedullary nail 100 can include an isolator 130 (shown in FIGS. 3 and 5) that comprises the third material 105. The third material 105 can form a barrier between the first material 101 and the second material 103. In some examples, the second material 103 can be at least partially encapsulated in the third material 105. For instance, in some examples, the second material 103 can be completely encapsulated in the third material 105. Stated differently, the third material 105 can at least partially or completely surround the second material 103. Thus, the wire that comprises the second material 103 can be at least partially or completely encapsulated in the isolator that comprises the third material 105. Similarly, in some embodiments, the third material 105 can be at least partially encapsulated in the first material 101. For instance, in some examples, the third material 105 can be completely encapsulated in the first material 101. Stated differently, the first material 101 can at least partially or completely surround the third material 105. Consequently, the third material 105 can be disposed between the first and second materials. Thus, the isolator that comprises the third material 105 can be at least partially or completely encapsulated in the implant grade material. The isolator can limit, or prevent altogether, any corrosion that might otherwise occur if the first and second materials were in contact with one another. In some embodiments, the third material 105 can be integral and monolithic with at least one, such as both, of the first and second materials. In other embodiments, the intramedullary nail 100 can include an insert that comprises the third material 105 and can be disposed in the intramedullary nail 100.

The wire 140 can include at least one coil 142. Each coil 142 can wrap around at least a portion of a respective one of the at least one bone-anchor locking holes 124. For example, each coil 142 can encircle or surround at least a portion of a respective one of the at least one bone-anchor locking holes 124. In at least some embodiments, each coil 142 can be substantially concentric with a respective one of the bone-anchor locking holes 124. Each coil 142 can be configured as a helical coil that produces an electromagnetic field as shown in FIG. 6 when the coil carries an electrical current, or can be any other suitable coil that produces an electromagnetic field when the coil carries an electrical current. Thus, each coil 142 can be considered to be an electromagnet. The at least one coil 142 can be supported by the nail body 102 such that a position of the at least one bone-anchor locking hole can be determined based on the magnetic field generated when an electrical current is carried through the coil 142.

As shown in FIG. 2, in some embodiments, each coil 142 can surround only a portion of a respective one of the at least one bone-anchor locking holes 124. The portion can be adjacent one of the first and second openings 124a and 124b. For example, each coil 142 can extend from one of the first and second openings 124a and 124b towards the other of the first and second openings 124a and 124b along the central axis $A_B$ of a respective one of the bone-anchor locking holes 124. Each coil 142 can terminate before the other of the first and second openings 124a and 124b. For example, each coil 142 can terminate before the cannula 120. In FIG. 2, each coil 142 terminates between the outer surface 114 and the interior surface 118. Thus, each coil 142 is encapsulated in the nail body 102, such as within the tubular wall 122 of the nail body 102, between the outer surface 114 and the interior surface 118.

In alternative embodiments, and with reference to FIGS. 4 and 5, each coil 142 can surround at least a middle portion of a respective one of the bone-anchor locking holes 124 that is midway between the first and second openings 124a and 124b of the respective one of the bone-anchor locking holes 124. In some such embodiments, each coil 142 can surround substantially an entirety of a respective one of the bone-anchor locking holes 124. For example, each coil 142 can extend from one of the first and second openings 124a and 124b to the other of the first and second openings 124a and 124b along the central axis $A_B$ of a respective one of the bone-anchor locking holes 124. However, it will be understood that each coil 142 can extend outward from the middle portion of a respective one of the bone-anchor locking holes 124 and terminate before the first and second openings 124a and 124b of the respective one of the bone-anchor locking holes 124.

Figure 17:
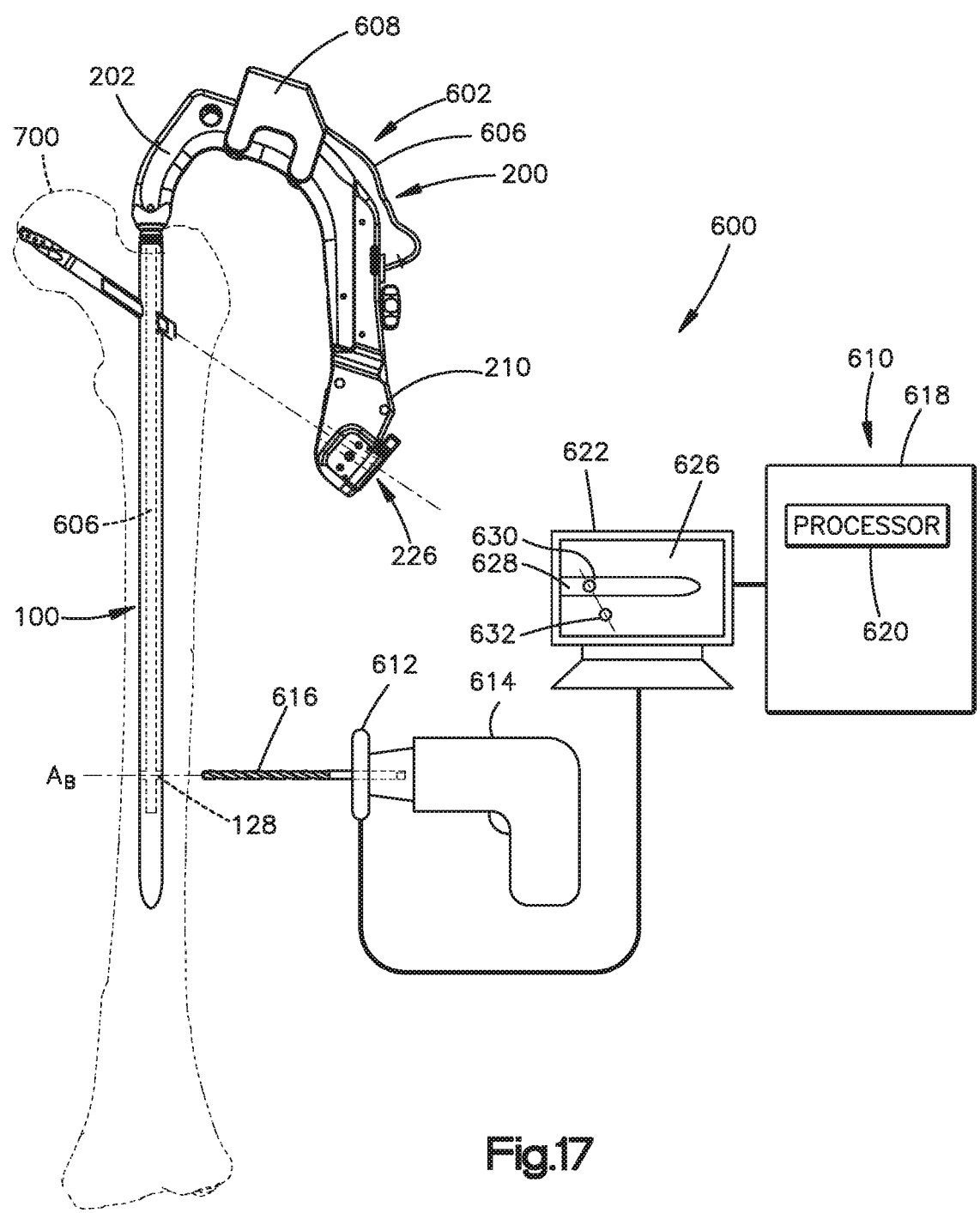
FIG. 17 shows a schematic diagram of an intramedullary nail that is disposed in a medullary canal of a bone and a targeting system configured to locate a bone-anchor locking hole of an intramedullary nail.

The at least one wire 140 can include a pair of input-output wires 144 that are configured to carry an electrical current between the at least one coil 142 and a power source (shown in FIG. 17). Note that an electrical current can be carried along either the clockwise or counterclockwise directions in FIGS. 2 and 4. The input-output wires 144 can be at least partially encapsulated in the first material 101. Note that portions of the input-output wires 144 are shown in dashed lines to indicate that they are hidden within material of the nail body 102. Thus, although the input-output wires 144 appear to extend through bone-anchor locking holes 124 in the schematic representations of FIGS. 2 and 4 (and through the cannulation 120 of FIG. 2), the wires 144 do not actually extend through the bone-anchor locking holes 124 (or the cannulation 120). Rather, the wires 144 are encapsulated in the nail body 102 at a location that does not intersect the bone-anchor locking holes 124 as shown in FIG. 3.

In some embodiments, the input-output wires 144 can extend from the proximal end 106 of the intramedullary nail 100, away from the distal end 104, such that they can be physically connected to the power source to provide an electrical current to the at least one coil 142. After bone anchors have been inserted into the bone-anchor locking holes 124, a cap or plug 148 can be coupled to the proximal end 106 of the nail 100 so as to cover the input-output wires 144, thereby preventing the wires 144 from coming into contact with the patient. In alternative embodiments (not shown), the input-output wires 144 do not extend from the proximal end 106. Rather, electrical contacts (not shown) of the power source can be inserted into the proximal end 106 of the intramedullary nail 100 and placed into physical contact with the input-output wires 144 so as to provide an electrical current to the at least one coil 142.

In some embodiments as shown in FIGS. 2 and 4, the intramedullary nail 100 can include a plurality of coils 142. In some such embodiments, the plurality of coils 142 can be connected in series with one another. For example, the at least one wire 140 can include at least one, such as a plurality, of connecting wires 146 that are configured to electrically connect the coils 142 to one another. Each connecting wire 146 can extend from a second (e.g., output) end 142b of one of the coils 142 to a first (e.g., input) end 142a. The first and second ends 142a and 142b of each coil 142 can be offset from one another along a respective one of the central axes $A_B$.

In alternative embodiments (not shown), at least one coil 142, up to all of the coils 142, can have its own input-output wires 144. In such embodiments, an electrical current can be carried to one of the coils 142 without carrying the electrical current all of the coils 142. In embodiments in which every coil 142 has its own input-output wires 144, the electrical current can be carried to each one of the coils 142 without carrying the electrical current any of the other coils 142.

Turning more specifically to FIG. 7, an intramedullary nail 100 can include at least one magnet 150 that is configured to generate a magnetic field. Each magnet 150 can be a permanent magnet. Each magnet 150 can be supported by the nail body 102 such that a position of the at least one bone-anchor locking hole 124 can be determined based on the magnetic field emitted by the magnet 150. For example, the position of the at least one bone-anchor locking hole 124 can be determined using a sensor such as a hall sensor that measures the magnetic field of the magnet 150. The magnet 150 can be formed of a second material 103, different from the first material 101. The second material 103 can be any suitable material that emits a magnetic field. The second material 103 can be formed of a non-biocompatible material if the second material 103 is encapsulated within the first material 101 so as to prevent the second material 103 from coming into contact with patient. Alternatively, the second material 103 can be biocompatible material if the second material 103 is exposed such that the second material 103 might come into contact with the patient.

As described above in relation to FIGS. 2-5, in at least some embodiments, the intramedullary nail 100 can comprise a third material 105, different from the first and second materials. For example, the intramedullary nail 100 in FIG. 7 can include an isolator (not shown in FIG. 7) that comprises the third material 105. The third material 105 can form a barrier between the first material 101 and the second material 103. In some examples, the second material 103 can be at least partially encapsulated in the third material 105. For instance, in some examples, the second material 103 can be completely encapsulated in the third material 105. Stated differently, the third material 105 can at least partially or completely surround the second material 103. Thus, each magnet 150 that comprises the second material 103 can be at least partially or completely encapsulated in the isolator that comprises the third material 105. Similarly, in some embodiments, the third material 105 can be at least partially encapsulated in the first material 101. For instance, in some examples, the third material 105 can be completely encapsulated in the first material 101. Stated differently, the first material 101 can at least partially or completely surround the third material 105. Consequently, the third material 105 can be disposed between the first and second materials. Thus, the isolator that comprises the third material 105 can be at least partially or completely encapsulated in the implant grade material. The isolator can limit, or prevent altogether, any corrosion that might otherwise occur if the first and second materials were in contact with one another.

Turning more specifically to FIG. 8, an intramedullary nail 100 can include at least one wire 140 that is configured to carry an electrical current. The at least one wire 140 can be supported by the nail body 102 such that a position of the at least one bone-anchor locking hole can be determined based on the flow of an electrical current through the wire 140. The wire 140 can be formed of a second material 103, different from the first material 101. The second material 103 can be formed of a non-biocompatible material if the second material 103 is encapsulated within the first material 101 so as to prevent the second material 103 from coming into contact with patient. Alternatively, the second material 103 can be biocompatible material if the second material 103 is exposed such that the second material 103 might come into contact with the patient.

The second material 103 can be, for example, a piezoelectric material. The piezoelectric material can generate an electrical current as the intramedullary nail 100 is bent during insertion of the nail 100 into the medullary canal. Alternatively, a resistance of the piezoelectric material can change as the intramedullary nail 100 is bent during insertion of the nail 100. The change in electrical current and/or resistance can be used to calculate a position of the at least one bone-anchor locking hole 124.

The wire 140 can have a pair of input-output wires 144 that extend from the proximal end 106 towards the distal end 104. The input-output wires 144 can extend to at least the distal portion 108 of the intramedullary nail 100. The input-output wires 144 can be elongate as they extend from the proximal end 106 towards the distal end 104. The input-output wires 144 can be substantially straight as then extend from the proximal end 106 towards the distal end 104. The wire 140 can also have a connecting wire 146 that connects distal ends of the input-output wires 144 to one another. Note that portions of the input-output wires 144 are shown in dashed lines to indicate that they are hidden within material of the nail body 102. Thus, although the wire 140 appears to extend through bone-anchor locking holes 124 and the cannulation 120 in the schematic representation of FIG. 8, the wire 140 does not actually extend through the bone-anchor locking holes 124 or the cannulation 120. Rather, the wire 140 is encapsulated in the nail body 102 at a location that does not intersect the bone-anchor locking holes 124 or the cannulation 120.

As described above, in at least some embodiments, the intramedullary nail 100 can comprise a third material 105, different from the first and second materials. For example, the intramedullary nail 100 in FIG. 8 can include an isolator 130 (not shown in FIG. 8) that comprises the third material 105. The third material 105 can form a barrier between the first material 101 and the second material 103. In some examples, the second material 103 can be at least partially encapsulated in the third material 105. For instance, in some examples, the second material 103 can be completely encapsulated in the third material 105. Stated differently, the third material 105 can at least partially or completely surround the second material 103. Thus, the wire that comprises the second material 103 can be at least partially or completely encapsulated in the isolator that comprises the third material 105. Similarly, in some embodiments, the third material 105 can be at least partially encapsulated in the first material 101. For instance, in some examples, the third material 105 can be completely encapsulated in the first material 101. Stated differently, the first material 101 can at least partially or completely surround the third material 105. Consequently, the third material 105 can be disposed between the first and second materials. Thus, the isolator that comprises the third material 105 can be at least partially or completely encapsulated in the implant grade material. The isolator can limit, or prevent altogether, any corrosion that might otherwise occur if the first and second materials were in contact with one another.

In some embodiments, the nail body 102 of the intramedullary nail 100 can be formed from the first material 101 having a first mechanical property, and another material having a mechanical property that is different from the first mechanical property. In one example, the other material can have a strength that is greater than that of the first material 101 so that the other material increases the strength of the intramedullary nail. In another example, the other material can have an elasticity that is different from that of the first material 101. The first material and the other material can be selected to personalize the biomechanical properties of the implant to the patient's need.

Turning now to FIGS. 9 to 12, a method according to one embodiment is shown of fabricating an intramedullary nail 100 that is sized and configured to be implanted into a medullary canal of a bone. The method comprises a step (FIG. 9) of forming a nail body 102 from a first material 101 that is biocompatible. As described above, the nail body 102 has a proximal end 106 (see e.g., FIG. 1), a distal end (see e.g., FIG. 1) that is offset from the proximal end, an outer surface 114 that extends from the proximal end to the distal end, and an inner surface 112 that defines at least one bone-anchor locking hole 124 that extends into the outer surface 114 and that is configured to receive a bone anchor to lock the intramedullary nail 100 in the medullary canal. The nail body 102 can be formed by any suitable manufacturing process, including (without limitation) machining, molding, casting, and additive manufacturing such as three-dimensional printing.

The method further comprises a step (FIGS. 10 to 12) of at least partially encapsulating a magnet 150 or an electrically conductive wire 140 formed from a second material 103, different from the first material 101, in the nail body 102 such that, when at least one of an electrical current and a magnetic field is produced by the magnet 150 or electrically conductive wire 140, a position of the at least one bone-anchor locking hole 124 can be detected based on the at least one of the electrical current and the magnetic field.

Figure 10:
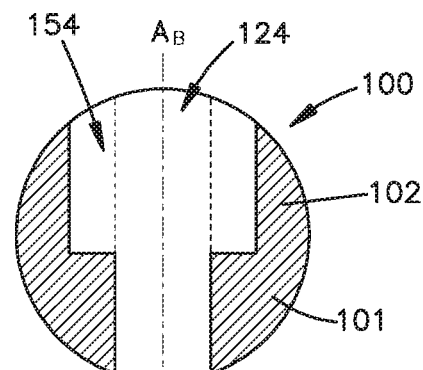
FIG. 10 shows a cross-sectional end view of the intramedullary nail of FIG. 9 with the bone-anchor locking hole enlarged to receive an electrically conductive wire or magnet.
Figure 11:
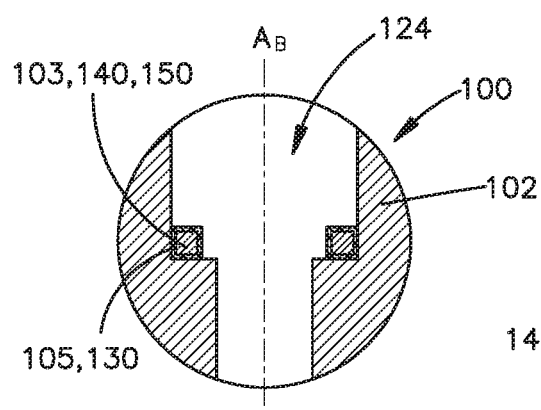
FIG. 11 shows a cross-sectional end view of the intramedullary nail of FIG. 10 in which an electrically conductive wire or magnet is inserted into the enlarged bone-anchor locking hole.
Figure 12:
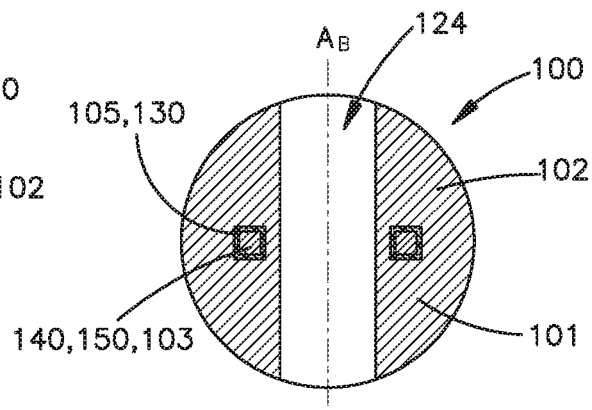
FIG. 12 shows a cross-sectional end view of the intramedullary nail of FIG. 11 during a fourth step of fabrication in which the electrically conductive wire or magnet is encased.

In one example, at least one void 154 can be formed in the nail body 102 as shown in FIG. 10. The second material 103, and optionally the third material 105, can be deposited onto a surface within the void 154 as shown in FIG. 11 so as to form the magnet 150 or electrically conductive wire 140 and optionally the isolator 130. In some embodiments, the second material 103, and optionally the third material 105, can be deposited onto a surface within the void 154 so as to form a coil 142. The second material 103, and optionally the third material 105, can be deposited using any suitable manufacturing process such as (without limitation) additive manufacturing such as three-dimensional printing. Thus, the magnet 150 or electrically conductive wire 140 can be formed using any suitable manufacturing process such as (without limitation) additive manufacturing such as three-dimensional printing. The depositing can be performed such that at least one of the second and third materials 103 and 105 is integral and monolithic with the first material 101. Further, the second and third materials 103 and 105 can be integral and monolithic with one another. The second material 103, and optionally the third material 105, can be at least partially encapsulated in the first material 101 as shown in FIG. 12 using any suitable manufacturing process such as (without limitation) additive manufacturing such as three-dimensional printing.

Figure 13:
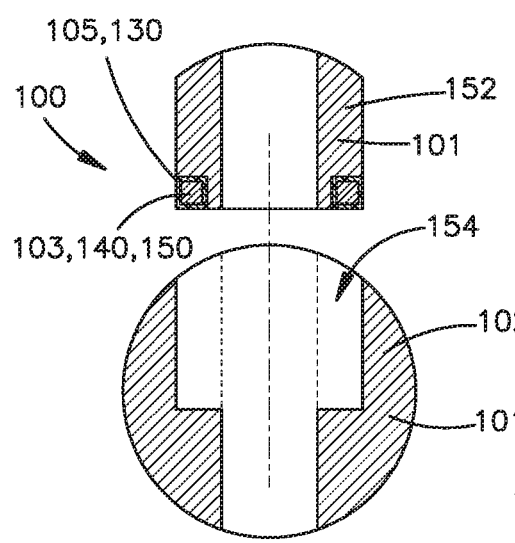
FIG. 13 shows a cross-sectional end view of an intramedullary nail according to another embodiment that is spaced from an insert having an electrically conductive wire or magnet.
Figure 14:
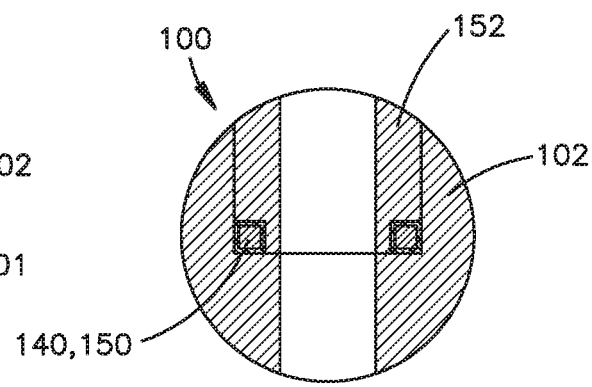
FIG. 14 shows a cross-sectional end view of the intramedullary nail of FIG. 13 with the insert disposed in a bone-anchor locking hole of the intramedullary nail.

Referring to FIGS. 13 and 14, a method according to another embodiment is shown of fabricating an intramedullary nail 100 that is sized and configured to be implanted into a medullary canal of a bone. The method comprises a step (FIG. 13) of forming a nail body 102 from a first material 101 that is biocompatible. As described above, the nail body 102 has a proximal end 106 (see e.g., FIG. 1), a distal end (see e.g., FIG. 1) that is offset from the proximal end, an outer surface 114 that extends from the proximal end to the distal end, and an inner surface 112 that defines at least one bone-anchor locking hole 124 that extends into the outer surface 114 and that is configured to receive a bone anchor to lock the intramedullary nail 100 in the medullary canal. The nail body 102 can be formed by any suitable manufacturing process, including (without limitation) machining, molding, casting, and additive manufacturing such as three-dimensional printing.

The method further comprises a step (FIG. 14) of at least partially encapsulating a magnet 150 or an electrically conductive wire 140 formed from a second material 103, different from the first material 101, in the nail body 102 such that, when at least one of an electrical current and a magnetic field is produced by the magnet 150 or electrically conductive wire 140, a position of the at least one bone-anchor locking hole 124 can be detected based on the at least one of the electrical current and the magnetic field.

The step of forming the nail body 102 can comprise forming at least one void 154 in the nail body 102 as shown in FIG. 13. The step of at least partially encapsulating a magnet 150 or an electrically conductive wire 140 can include forming an insert 152 that comprises the second material 103, and optionally at least one of the first material 101 and the third material 105. For example, the insert 152 can comprise the second material 103 encapsulated in the first material 101. Optionally, the insert 152 can comprise the second material 103 encapsulated in the third material 105. The insert can be formed by any suitable manufacturing process, including (without limitation) machining, molding, casting, and additive manufacturing such as three-dimensional printing. The step of at least partially encapsulating a magnet 150 or an electrically conductive wire 140 can include disposing the insert in the void 154.

Figure 15:
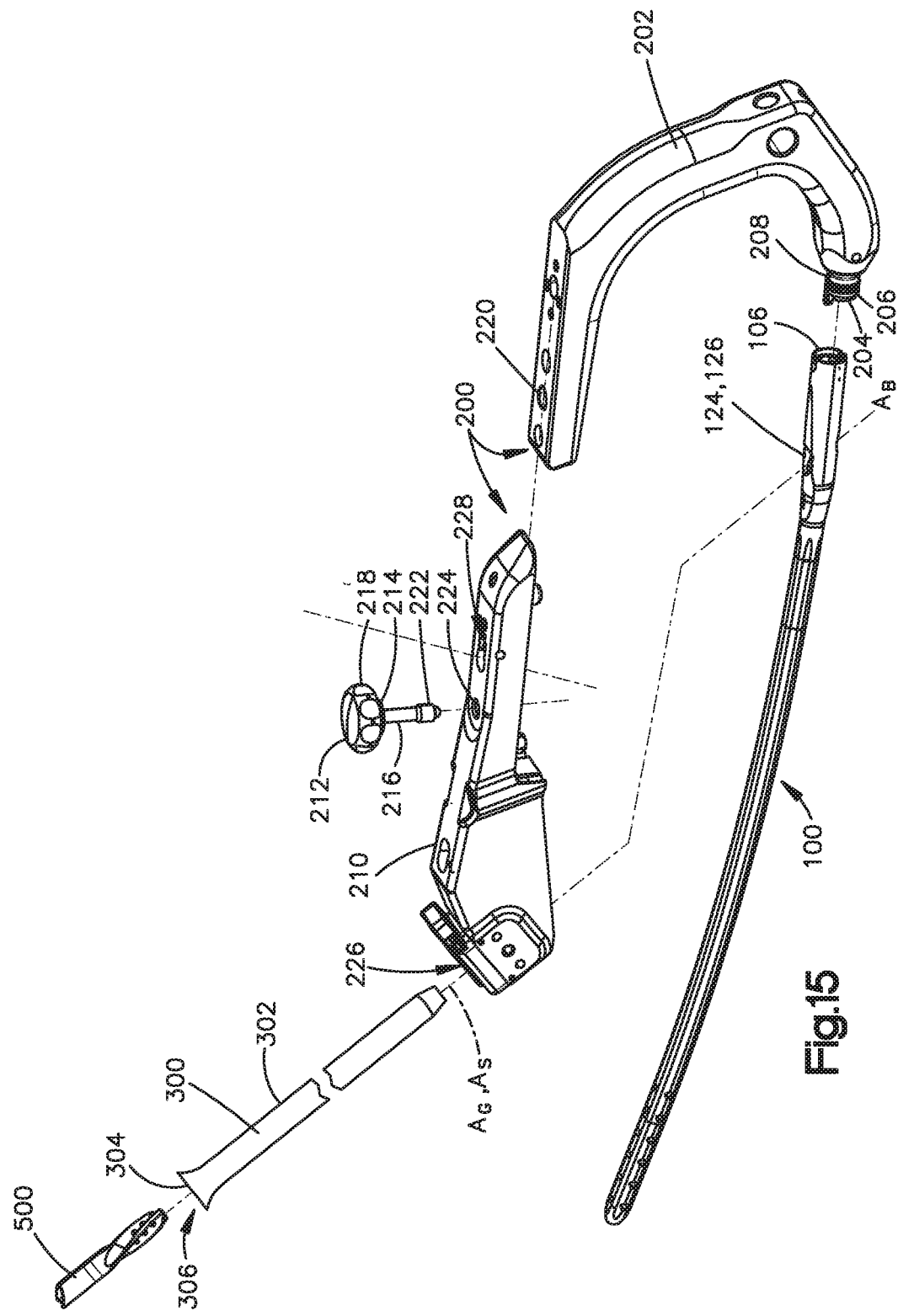
FIG. 15 shows an exploded perspective view of an intramedullary nail with an aiming system according to one embodiment.
Figure 16:
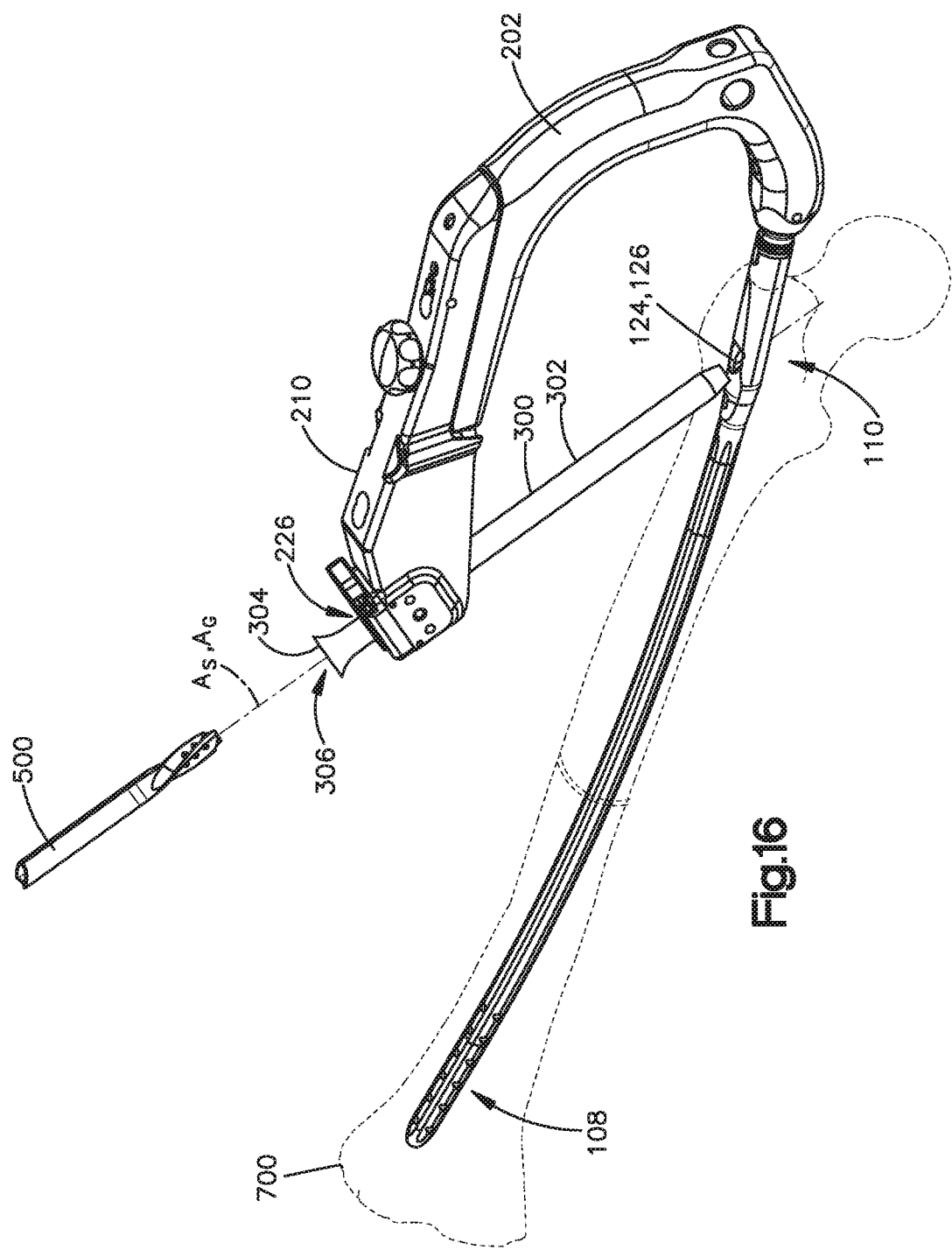
FIG. 16 shows a perspective view of an intramedullary nail that is disposed in a medullary canal of a bone, and an aiming system attached to intramedullary nail and supporting a bone-anchor aiming sleeve receiving a drill bit.

Turning now to FIG. 15, an intramedullary nail insertion system is shown with an intramedullary nail 100, an aiming system 200, and a targeting instrument 602. The aiming system 200 can include any combination of one or more, up to all, of (i) a handle 202, (ii) an aiming arm 210, and (iii) a bone-anchor aiming sleeve 300. The aiming system 200 is configured to align tools or instruments with at least one proximal bone-anchor locking hole 126. For example, when the aiming system 200 is attached to the intramedullary nail 100, the aiming system 200 can align at least one of a drill bit (not shown) and a bone anchor 500 with the at least one proximal bone-anchor locking hole 126 so as to guide the at least one of a drill bit (not shown) and the bone anchor 500 towards the at least one proximal bone-anchor locking hole 126. The bone anchor 500 can be a locking screw or any other suitable bone anchor. Although one embodiment of an aiming system 200 is shown, it will be understood that other configurations of aiming systems can be employed. For instance, at least one of the handle 202 and aiming arm 210 can be configured in a manner other than that shown.

The handle 202 is configured to be held by an operator (human or machine) as the operator guides and forces the intramedullary nail 100 into the medullary canal of the bone. The handle 202 can include a connection end 204 configured to connect to the proximal end 106 of the intramedullary nail 100. The connection end 204 can include an engagement feature configured to couple to an engagement feature at the proximal end 106 of the intramedullary nail 100. For example, in one embodiment, the engagement feature of the handle 202 can include a shaft 206 having external threading 208 thereon, and the engagement feature of the intramedullary nail 100 can include internal threading 134 (see FIG. 2) on the interior surface 118 of the cannulation 120 of the intramedullary nail 100 at the proximal end 106. The shaft 206 can be sized and configured to be received in the cannulation 120 at the proximal end 106 of the intramedullary nail 100 such that the external threading 208 engages the internal threading 134 of the intramedullary nail 100. In alternative embodiments, the engagement features of the handle 202 and the intramedullary nail 100 can be engagement features other than the internal and external threading shown, the other engagement features being suitable for coupling the handle 202 to the intramedullary nail 100.

The at least one aiming arm 210 can be fixedly or removably attached to the handle 202 via any suitable fastener. Alternatively, the handle 202 can be monolithic with the aiming arm 210 such that the handle 202 and aiming arm 210 form a one-piece structure. The aiming system 200 can include a coupler 212 that removably attaches the aiming arm 210 to the handle 202. In one embodiment, the coupler 212 can have an abutment surface 214 and a shaft 216 that extends from the abutment surface 214 to a distal end of the shaft 216. The abutment surface 214 can be defined by a handgrip 218. The shaft 216 can have an engagement feature configured to engage an engagement feature of a bore 220 of the handle 202. Further, the shaft 216 is sized and configured to extend through a bore 224 of the aiming arm 210 into the bore 222 of the handle 202 such that the aiming arm 210 is trapped between the abutment surface 214 and the handle 202. In one example, the engagement feature of the shaft 216 can be external threading and the engagement feature of the bore 220 can be internal threading that is configured to engage the external threading of the shaft 216.

The aiming system 200 can define a guide hole 226 that is configured to guide at least one a drill bit (not shown) and the bone anchor 500 towards at least one proximal bone-anchor locking hole 126. The guide hole 226 can have a central axis $A_G$ that is substantially aligned with the central axis $A_B$ of the at least one proximal bone-anchor locking hole 126 when the aiming system 200 is attached to the intramedullary nail 100.

The bone-anchor aiming sleeve 300 has a tubular body that includes an outer surface 302 and an inner surface 304. The outer surface 302 defines an outer perimeter of the sleeve 300 and is sized and configured to conform to the guide hole 226. The inner surface 304 is opposite the outer surface 302 and defines a cannulation 306 that extends entirely through the sleeve 300. The cannulation 306 is sized to receive at least one of a drill bit (not shown) and the bone anchor 500. When the sleeve 300 is received in the guide hole 226 and the aiming system 200 is attached to the intramedullary nail 100, a central axis As of the sleeve 300 can be substantially aligned with the central axis $A_G$ of the guide hole 226 and the central axis $A_B$ of the at least one proximal bone-anchor locking hole 126. As such, the sleeve 300 is positioned and configured to guide at least one of a drill bit (not shown) and the bone anchor 500 towards the at least one proximal bone-anchor locking hole 126. It will be understood that, in alternative embodiments, the sleeve 300 can be integral with the aiming arm 210 or can be omitted.

Referring briefly to FIG. 17, embodiments of the disclosure can include a targeting system 600 that is configured to detect a location of at least one of a proximal bone-anchor locking hole 126 and a distal bone-anchor locking hole 128 hidden beneath the surface of the bone 700. For example, the targeting system 600 can be configured to sense at least one of an electrical current and a magnetic field in the intramedullary nail 100, and detect a location of the at least one bone-anchor locking hole 124 based on the at least one of the electrical current and the magnetic field. The targeting system 600 can optionally include a device 608 that is in electrical communication with at least one wire 140 of the intramedullary nail 100 (in embodiments that implement at least one wire 140). The device 608 can be supported by the handle 202 as shown; however, embodiments of the disclosure are not so limited. The device 608 can include a power source that provides power to the at least one wire 140. For example, the device 608 can be physically connected to the at least one wire 140 via a cable 606 or other suitable electrical contact.

Additionally or alternatively, the device 608 can include a wireless communicator that is configured to communicate with a computing device 610 positioned outside of the body. For example, the device 608 can include an antenna (not shown), a communications circuit (not shown) coupled to the antenna, and a power source such as a battery that can power at least one of the device 608 and the at least one wire 140. In alternative embodiments, the at least one wire 140 can be connected to the computing device 610 via a cable such that communications between the at least one wire 140 and the computing device 610 occur over the cable rather than wirelessly. In yet other embodiments, at least one of the power source and the communicator of the device 608 can be omitted. For example, a power source is not needed to power the magnets 150 in the example nail 100 of FIG. 7. As another example, the at least one wire 140 can be powered by an external device (e.g., 612) that wirelessly transmits power through the bone 700 to the at least one wire 140 so as to cause a current to flow through the wire 140.

The targeting system 600 can include at least one of the computing system 610, a landmark identifier 612, and a cutting instrument 614 such as a drill having a drill bit 616. The computing system 610, a landmark identifier 612, and a cutting instrument 614 can be implemented as described in U.S. Pat. No. 8,623,023, the teachings of which are hereby incorporated by reference as if set forth in their entirety herein. The landmark identifier 612 is configured to detect a location of at least one of a proximal bone-anchor locking hole 126 and a distal bone-anchor locking hole 128. The landmark identifier 612 can include one or more sensors (such as inductive sensors) or can include a field generator that includes one or more induction coils that generate an electromagnetic field. The computing system 610 can include a processor 620 and a feedback device 622 that provides to the user at least one of (i) a visual feedback (e.g., via a monitor or lights), (ii) an audio feedback (e.g., via a speaker), and (iii) a tactile feedback. The processor 620 and the feedback device 622 can be implemented separately or the feedback device 622 can be implemented in a shared housing 618 with the processor 620.

Turning now to FIGS. 15 to 18, a method 800 of implanting the intramedullary nail 100 will now be described. In step 802 of FIG. 10, the intramedullary nail 100 is inserted into the medullary canal of a bone 700 such that the intramedullary nail 100 is elongate along the medullary canal from the leading portion 108 of the intramedullary nail 100 to the trailing portion 110 of the intramedullary nail 100 as shown in FIG. 7. In one embodiment, the handle 202 of the aiming system 200 is coupled to the proximal end 106 of the intramedullary nail 100, and the operator holds onto the handle 202 to drive the intramedullary nail 100 into the medullary canal of the bone 700. The aiming arm 210 can be attached to the handle 202 before or after the nail 100 is driven into the bone.

Optionally, in step 804, a proximal bone anchor 500 can be inserted into at least one proximal bone-anchor locking hole 126 such that the proximal bone anchor 500 extends through the cannulation 120 of the intramedullary nail 100. In embodiments that employ a cannulation 120, the bone anchor 500 may intersect the cannulation 120, thereby at least partially obstructing the proximal end of the cannulation 120. According to one embodiment, step 804 can be performed as follows and with reference to FIG. 16. The aiming arm 210 is attached to the handle 202 (if not already attached). The bone-anchor aiming sleeve 300 is received in the guide hole 226 of the aiming system 200 such that the central axis As of the sleeve 300 is substantially aligned with both the central axis $A_G$ of the guide hole 226 and the central axis $A_B$ of the at least one proximal bone-anchor locking hole 126. A cut is made in the skin of the patient (before or after receiving the sleeve 300) at a point where the central axis $A_G$ of the guide hole 226 intersects the skin, and the sleeve 300 can be advanced into the skin towards the bone 700. A cutting instrument, such as a drill bit 616 of a drill 616 (shown in FIG. 17), can then be inserted into the bone-anchor aiming sleeve 300 and guided towards the proximal bone-anchor locking hole 126 so as to cut a bore that extends into the bone to the proximal bone-anchor locking hole 126. A bone anchor 500 such as a locking screw or other suitable bone anchor is driven through the bore in the bone and into the proximal bone-anchor locking hole 126 so as to secure the proximal end 106 of the intramedullary nail 100 to the bone 700. Note that, in alternative embodiments, step 804 can be performed after inserting a bone anchor into the at least one distal bone-anchor locking hole 128.

Figure 18:
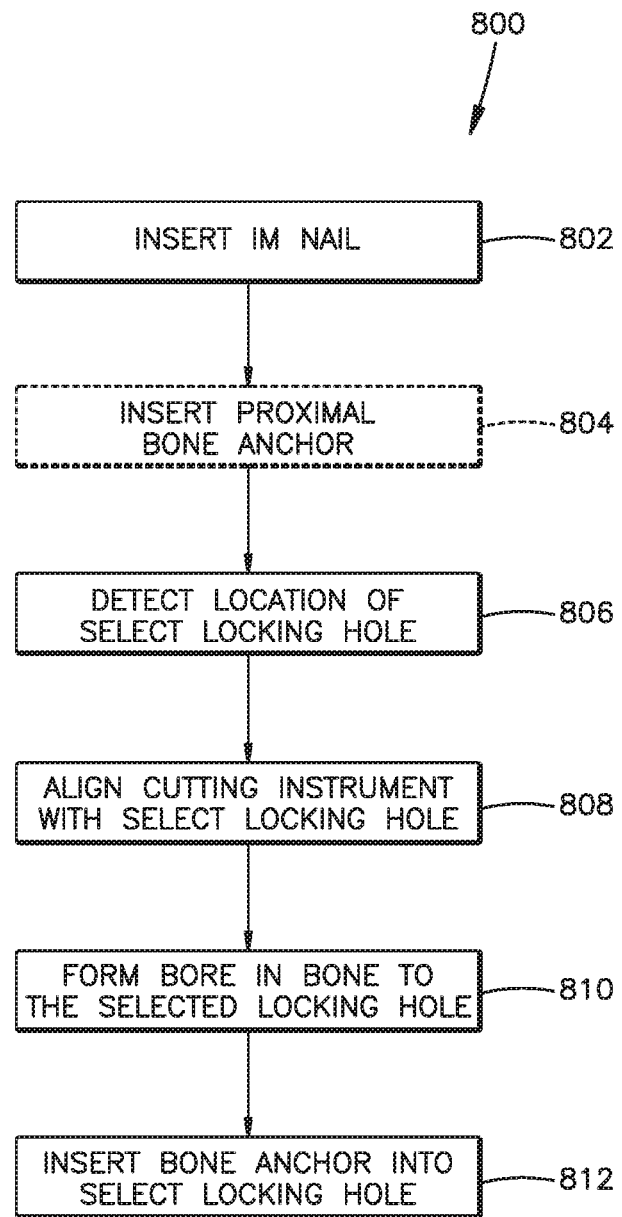
FIG. 18 shows a simplified flow diagram of a method of implanting an intramedullary nail according to one embodiment.

In step 806, and with reference to FIGS. 17 and 18, a location of a select one of the locking holes 124, such as a distal bone-anchor locking hole 128, is detected based on at least one of an electrical current and a magnetic field produced by the intramedullary nail 100. The location can be detected in any suitable manner. In the following description, several example methods for detecting the location of the locking hole is described; however, it will be understood that other methods are possible.

In one example, and with reference to the embodiments of FIGS. 2-5, a power supply (e.g., 608 in FIG. 17) can provide an electrical current to the at least one wire 140. As the electrical current is carried through the at least one wire 140, each of the coils 142 emits an electromagnetic field as shown in FIG. 6. In another example, the landmark identifier 612 can generate an electromagnetic field and apply the electromagnetic field to the intramedullary nail 100, thereby causing a current to generated in the at least one wire 140. In yet another example, and with reference to the embodiment of FIG. 7, each permanent magnet 150 emit a magnetic field.

In each of these examples, and with reference to FIG. 17, the landmark identifier 612 senses the electrical current or magnetic field for the select coil 142 or magnet 150, and communicates information about the electrical current or magnetic field to the processor 620 in the form of an electrical signal. The processor 620 determines, based on the electrical signal, a position of the landmark identifier 612 relative to the select coil 142 or magnet 150. For example, the processor 620 can determine at least one of (i) a distance of the landmark identifier 612 from the select coil 142 or magnet 150 with respect to a radial direction, (ii) a distance of the landmark identifier 612 from the select coil 142 or magnet 150 with respect to the longitudinal direction L, and (iii) an angular orientation the landmark identifier 612 relative to the select coil 142 or magnet 150.

The processor 620 can compare information derived from the select coil 142 or magnet 150 with reference values associated the landmark identifier 612 to determine differences between the derived values and the reference values. The processor 620 can use these determined differences between the derived values and reference values to determine a difference in position and orientation of the landmark identifier 612 from the select coil 142 or magnet 150. The processor 620 can determine a current position and orientation of the landmark identifier 612 relative to the select coil 142 or magnet 150 based on the differences.

The processor 620 can use the current distance and orientation of the landmark identifier 612 relative to the select coil 142 or magnet 150 to determine the current distance of the landmark identifier 612 from the corresponding bone-anchor locking hole 124 and the current orientation of the landmark identifier 612 relative to the corresponding bone-anchor locking hole 124. For example, the processor 620 can determine the current distance and relative orientation of the landmark identifier 612 relative to the corresponding bone-anchor locking hole 124 based on a known position and orientation of the bone-anchor locking hole 124 relative to the select coil 142 or magnet 150. The processor 620 also determines a current position of the drill 614, including the drill bit 616, from the bone-anchor locking hole 124 as well as a current orientation of the drill 614 and the drill bit 616 relative to the central axis AH of the bone-anchor locking hole 124 based on a known position and orientation of the drill 614 and the drill bit 616 relative to the location of the landmark identifier 612.

With continued reference to FIGS. 17 and 18, in step 808, the cutting instrument is aligned with the select locking hole 124 based on the detected location of the select locking hole 124. In so doing, the position of the select locking hole and the angulation of the locking hole can be determined by moving the cutting instrument such that a central axis of the cutting instrument is aligned with the central axis $A_B$ of the select locking hole 124. The cutting instrument and select locking hole 124 can be aligned using feedback generated by the processor 620 and provided to the operator by the feedback device 622. For example, the processor 620 of the computing device 610 can generate a graphical user interface based on the determined current position and orientation of the drill 614 and the drill bit 616 relative to the bone-anchor locking hole 124, or based on a current position and orientation of another tool relative to another landmark. The graphical user interface can include a representative image 628 of the intramedullary nail 100 that includes a representative image 630 of the select bone-anchor locking hole 124. The graphical user interface can also include a representation 632 of the drill bit 616. The operator can move the drill 614 relative to the select bone-anchor locking hole 124 until the representative images 628 and 630 of the intramedullary nail 100 and drill bit 616 are aligned. In alternative embodiments, the feedback device can provide instructions via an audio signal or lights (e.g., lighted arrows) to instruct the operator which direction(s) to move the drill 614 to align the drill bit 616 with the select locking hole.

In step 810, a bore is cut into the bone 700 with the cutting instrument 614 such that the bore extends to the select locking hole. Preferably, the bore is substantially coaxial with the select locking hole 124. In cutting the bore, the cutting instrument 614 can be advanced into the bone 700 a select distance. The select distance can be predetermined or can be determined during the operation. For example, the select distance can be determined based on relative positions of the cutting instrument 614 and the select bone-anchor locking hole 124 (as determined from the position of the select coil 124 or magnet 150). Alternatively, the cutting instrument 614 can be provided with a stop or markings that can be used to determine when the cutting instrument 614 has advanced a predetermined distance.

Prior to cutting the bore, an incision can be made in the skin at the location of the select locking hole. Additionally, a guide sleeve can be inserted into the incision towards the bone 700, and the guide sleeve can receive the cutting instrument 614 as the cutting instrument cuts the bore so as to prevent the cutting instrument 614 from damaging soft tissue. After cutting the bore in the bone 700, a bone anchor 502 (FIG. 8) is inserted through the bore in step 816 and into the select locking hole 124 so as to secure the intramedullary nail 100 to the bone 700. Steps 806 to 812 can be repeated for one or more additional bone anchors that are to lock the intramedullary nail 100 to the bone 700.

While certain example embodiments have been described, these embodiments have been presented by way of example only and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

What is claimed:

1. An intramedullary nail sized and configured to be implanted into a medullary canal of a bone, the intramedullary nail comprising:
   a nail body having:
      a proximal end and a distal end that are offset from one another such that the nail body is elongate from the proximal end to the distal end;
      an outer surface that extends from the proximal end to the distal end such that the outer surface defines a perimeter of the nail body; and
      an inner surface that defines at least one bone-anchor fixation hole that extends into the outer surface and that is configured to receive a bone anchor to lock the intramedullary nail in the medullary canal, wherein the nail body is formed from a first material that is biocompatible;
   a second material that is different from the first material and configured to produce at least one of an electrical current and a magnetic field; and
   a third material, different from the first and second materials, the third material being electrically insulative,
   wherein the second and third materials are supported by the nail body such that 1) the second material has at least a portion thereof that is encapsulated in the third material such that the third material surrounds the portion of the second material in a cross-sectional plane, 2) the first material surrounds the third material in the cross-sectional plane, 3) the first and third materials extend between the bone-anchor fixation hole and the portion of the second material along a radial direction that extends radially from the bone-anchor fixation hole, and 4) a position of the at least one bone-anchor fixation hole can be detected based on the at least one of the electrical current and the magnetic field.

2. The intramedullary nail of claim 1, wherein the second material surrounds at least a portion of the least one bone-anchor fixation hole.

3. The intramedullary nail of claim 2, wherein the first material defines the at least one inner surface, and the second material surrounds the at least one inner surface.

4. The intramedullary nail of claim 1, comprising at least one wire that is formed from the second material, the at least one wire extending between the proximal and distal ends.

5. The intramedullary nail of claim 4, wherein the at least one wire comprises at least one coil formed from the second material, the at least one coil helically surrounding at least a portion of the at least one bone-anchor fixation hole.

6. The intramedullary nail of claim 5, wherein the at least one coil is configured to emit an electromagnetic field when a current is carried through the at least one coil.

7. The intramedullary nail of claim 1, comprising a permanent magnet that surrounds at least a portion of the at least one bone-anchor fixation hole.

8. The intramedullary nail of claim 1, wherein the second material is integral and monolithic with at least one of the first material and the third material.

9. The intramedullary nail of claim 1, comprising an insert that comprises the second material.

10. The intramedullary nail of claim 1, wherein the second material is a piezoelectric material.

11. The intramedullary nail of claim 1, wherein the second material is at least partially encapsulated in the first material such that the second material is fixedly attached to the first material.

12. An intramedullary nail insertion system, comprising:
the intramedullary nail of claim 1; and
a targeting system comprising a sensor that is configured to sense at least one of an electrical current and a magnetic field in the intramedullary nail, and detect a location of the at least one bone-anchor fixation hole based on the at least one of the electrical current and the magnetic field.

13. A method of implanting an intramedullary nail into a bone, the method comprising steps of:
inserting the intramedullary nail of claim 1 into a medullary canal of the bone such that the intramedullary nail is elongate along the medullary canal from a proximal end of the intramedullary nail to a distal end of the intramedullary nail;
detecting a location of a select bone-anchor fixation hole that extends into the intramedullary nail by sensing at least one of an electrical current and a magnetic field produced by the second material;
aligning a cutting tool with the select fixation hole based on the detected location, the cutting tool having a cutting edge;
forming a bore in the bone with the cutting tool such that the bore extends to the select bone-anchor fixation hole; and
inserting a bone anchor through the bore and into the select bone-anchor fixation hole so as to secure the intramedullary nail to the bone.

14. The method of claim 13, wherein the select bone-anchor fixation hole is a distal bone-anchor fixation hole that extends into the intramedullary nail at a distal portion of the intramedullary nail, and the method comprises inserting a bone anchor through a proximal bone-anchor fixation hole that extends into the intramedullary nail at a proximal portion of the intramedullary nail before the sensing step.

15. The method of claim 13, wherein the sensing step comprises causing an electrical current to be carried by at least one wire embedded in the intramedullary nail.

16. The method of claim 15, wherein the causing step comprises causing the electrical current to be carried through a coil of the at least one wire that surrounds the select bone-anchor fixation hole such that the coil emits a magnetic field.

17. The method of claim 13, wherein the sensing step comprises sensing a magnetic field of a permanent magnet that surrounds at least a portion of the select bone-anchor fixation hole.

18. A method of fabricating an intramedullary nail that is sized and configured to be implanted into a medullary canal of a bone, the method comprising:
forming a nail body from a first material that is biocompatible such that the nail body has a proximal end, a distal end that is offset from the proximal end, an outer surface that extends from the proximal end to the distal end, and an inner surface that defines at least one bone-anchor fixation hole that extends into the outer surface and that is configured to receive a bone anchor to lock the intramedullary nail in the medullary canal; and
encapsulating, while forming the nail body, at least a portion of a second material in a third material such that the portion of the second material is surrounded by the third material in a cross-sectional plane, the second material being different from the first material and configured to produce at least one of an electrical current and a magnetic field, and the third material being different from the first and second materials and being electrically insulative; and
encapsulating, while forming the nail body, the third material in the first material such that 1) the first material surrounds the third material in the cross-sectional plane, 2) the first and third materials extend between the portion of the second material and the bone-anchor fixation hole along a radial direction that extends radially from the bone-anchor fixation hole, and 3) when at least one of an electrical current and a magnetic field is produced by the magnet or electrically conductive wire, a position of the at least one bone-anchor fixation hole can be detected based on the at least one of the electrical current and the magnetic field.

19. The method of claim 18, wherein the step of encapsulating the second material comprises forming a magnet or electrically conductive wire through additive manufacturing.

* * * * *